United States Patent
Marrs

[11] Patent Number: 6,115,452
[45] Date of Patent: Sep. 5, 2000

[54] X-RAY RADIOGRAPHY WITH HIGHLY CHARGED IONS

[75] Inventor: Roscoe E. Marrs, Livermore, Calif.

[73] Assignee: The Regents of the University of California, Oakland, Calif.

[21] Appl. No.: 09/186,875

[22] Filed: Nov. 4, 1998

Related U.S. Application Data

[60] Provisional application No. 60/070,810, Jan. 8, 1998.

[51] Int. Cl.[7] ..................................................... G21G 4/00
[52] U.S. Cl. ........................................... 378/119; 378/120
[58] Field of Search ...................................... 378/119, 120

[56] References Cited

U.S. PATENT DOCUMENTS

| | | | |
|---|---|---|---|
| 4,287,425 | 9/1981 | Elliott, Jr. .............................. | 250/445 T |
| 4,887,604 | 12/1989 | Shefer et al. ............................ | 128/654 |
| 4,929,839 | 5/1990 | Parker et al. ........................ | 250/492.3 |
| 5,063,294 | 11/1991 | Kawata et al. ............................ | 250/309 |
| 5,327,475 | 7/1994 | Golovanivsky et al. ................. | 378/34 |
| 5,398,273 | 3/1995 | Jordan et al. ............................. | 378/44 |
| 5,528,034 | 6/1996 | Yamazaki et al. ....................... | 250/309 |
| 5,596,620 | 1/1997 | Canistraro et al. ....................... | 378/84 |
| 5,712,483 | 1/1998 | Boone et al. ............................ | 250/367 |
| 5,849,093 | 12/1998 | Andrä .................................... | 134/1.3 |

OTHER PUBLICATIONS

S. Rondot and J. Cazaux, "Quantitative mapping of species moving in solution by x-ray projection microscopy," Rev. Sci. Instrum. 68 (4), Apr. 1997, pp. 1787–1791.

C. Kunz, "X–Ray Microscopy," Physica Scripta. vol. T61, 1996, pp. 19–25.

Roscoe Marrs et al, "The Electron–Beam Ion Trap," Physics Today, Oct. 1994, pp. 27–34.

R. E. Marrs et al., Rev. Sci. Instrum. 69, 204 (1998).

B. D. Cullity, Elements of X–ray Diffraction (Reading, MA: Addison–Wesley, 1978), pp. 19–21.

*Primary Examiner*—David V. Bruce
*Assistant Examiner*—Allen C. Ho
*Attorney, Agent, or Firm*—Alan H. Thompson

[57] ABSTRACT

An extremely small (1–250 micron FWHM) beam of slow highly charged ions deexciting on an x-ray production target generates x-ray monochromatic radiation that is passed through a specimen and detected for imaging. The resolution of the x-ray radiograms is improved and such detection is achieved with relatively low dosages of radiation passing through the specimen. An apparatus containing an electron beam ion trap (and modifications thereof) equipped with a focusing column serves as a source of ions that generate radiation projected onto an image detector. Electronic and other detectors are able to detect an increased amount of radiation per pixel than achieved by previous methods and apparati.

52 Claims, 4 Drawing Sheets

X-RAY RADIOGRAPHY WITH HIGHLY CHARGED IONS

This application claims priority in provisional application filed on Jan. 8, 1998, the first entitled "PROJECTION X-RAY MICROSCOPE POWERED BY HIGHLY CHARGED IONS," U.S. Ser. No., 60/070,810, by inventor Roscoe E. Marrs.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates generally to the field of radiography with mammography, vascular imaging, and x-ray microscopy being particular examples. More particularly, this invention relates to a new and improved method and apparatus for conducting internal biological imaging, industrial imaging, or microscopic imaging.

2. Description of Related Art

Medical and industrial x-ray imaging typically use a conventional x-ray tube for x-ray production. The spectrum of x-ray energies emitted from an x-ray tube is very broad. However, a much narrower range of x-ray energies is advantageous for many applications. Typically, a conventional film or screen-film system is used for x-ray detection. In some applications, fluorescent screens are used to convert x-ray images to visible light that can be captured with a camera. A relatively new x-ray detection technique is the use of electronic x-ray imaging detectors to obtain digital images. The quality of an x-ray image and the radiation dose required to obtain it are determined by the characteristics of the x-ray detector and the x-ray source working together.

One very common medical procedure is mammography, which is used for the diagnosis of breast cancer. In mammography, radiologists look for small features called microcalcifications. Because the features are small, a higher resolution x-ray film is used as compared to general radiography, and an x-ray tube with a small source size is required to avoid blurring of the image. The quality of the mammography image is degraded by x-ray scattering, and an anti-scatter grid is often required to preserve image quality. A modified mammography procedure for more detailed examination of a smaller area, referred to as cone projection, places even more stringent requirements on the x-ray source size and film resolution. A relatively high x-ray dose is required to resolve small abnormalities.

The diagnostic effectiveness of mammography is limited by the difficulty of distinguishing abnormal features from the features of normal breast tissue. Research has shown that monoenergetic radiation of, for example, approximately 17 to 20 keV, is more effective than broad band radiation for distinguishing abnormal features. Filters are used to reduce the energy spread of radiation from conventional x-ray tubes. Research has also shown that the comparison of x-ray images obtained at two different x-ray energies is effective for distinguishing abnormal features due to different changes in the absorption properties of calcifications and normal tissue at different x-ray energies.

Monoenergetic x-ray radiation, can be generated from several types of sources. Examples of previously considered narrow band x-ray sources include: the use of a Bragg-crystal monochromator, fluorescence x-rays from a secondary target, laser produced x-rays, x-rays produced from Compton backscattering on an electron beam, x-rays excited in a target by a proton beam, channeling radiation, and synchrotron radiation. Such sources have disadvantages that prevent their widespread use for radiography. For example, recent studies have shown that improved radiographic images can be obtained by using the very bright monochromatic radiation generated from synchrotron facilities. However, the present availability of synchrotron facilities, and concomitant cost thereof is far too limiting for general medical use.

One example of a common vascular imaging procedure is coronary angiography, which is used to image the arteries in the heart. In this procedure, a contrast agent (usually an iodine compound) is injected into a blood vessel to make the blood vessel visible in an x-ray image. Unfortunately, this is a dangerous procedure since it requires that a catheter be employed for injection of the contrast agent. The catheter is inserted into a peripheral artery and then threaded up to the heart so that the catheter tip is at the entrance of a coronary artery.

If the need for the arterial catheter in coronary angiography could be eliminated, then x-ray imaging could be done with greatly reduced risk. The risk could be reduced by injecting the contrast agent into a vein. However, the image quality is seriously degraded with a venous injection of the contrast agent because the contrast agent is diluted by about 20:1 by the time it has gone through the lungs and both sides of the heart and starts to fill the coronary arteries. Differential angiography, in which x-ray images acquired at two different x-ray energies are subtracted, is required to resolve the coronary arteries with venous injection of a contrast agent. Differential angiography has been demonstrated with synchrotron radiation, but such facilities are not available or suitable for general use.

X-ray microscopy provides information unobtainable with visible-light microscopy due to the different absorption properties of x-rays and the possibility of imaging smaller structures. As the capabilities of x-ray microscopes improve, they are becoming valuable tools in biology and materials science. High quality x-ray microscope images can be obtained with synchrotron radiation. However, there is a need for smaller and less expensive facilities for x-ray microscopy. One possible solution to this problem is projection x-ray microscopy. However, the performance of such devices is presently limited by the characteristics of available x-ray sources.

In general, it is difficult to realize all the desired features of radiography at the same time. For example, the use of a thicker and larger x-ray detection medium in order to achieve increased detection efficiency generally degrades the image resolution. The use of energy filters with a conventional x-ray tube in order to narrow the energy spectrum of the x rays generally requires a higher power x-ray tube, and undesirable radiation at other energies leaks through the filters. There is a need for a method to obtain x-ray images with monochromatic radiation at dual energies with high spatial resolution, good contrast, high detection efficiency, and low dose. The present invention satisfies these needs.

SUMMARY OF THE INVENTION

In the present invention, a source of monochromatic x rays is provided from the radiative deexcitation of slow highly charged ions to obtain an x-ray radiograph of an object by projection onto an x-ray imaging detector, particularly an electronic detector. An apparatus of the invention includes (1) an electron beam ion trap (EBIT) or other such electron beam ion source (EBIS) capable of generating slow highly charged ions that strike a solid target surface to produce characteristic x-ray line radiation in a narrow energy band, and (2) an imaging detector of such projected radiation. Such an apparatus allows the x-ray energies to be changed by switching to an ion with a different atomic number. The x-ray source can be localized to a relatively small area of cross-section, usually from above 0.1 to less than 500 microns full width at half maximum (FWHM) and often smaller than the resolution of the detector.

In the method of the invention, x rays are passed into a specimen and a magnified image of the interior of the specimen is projected onto an imaging detector. Since most electronic imaging detectors require large pixel size to achieve high efficiency, magnified images of objects achieve higher resolution at a given dosage of x-rays to the specimen and/or require a lower dosage for a given resolution. The method of the invention is particularly effective in x-ray microscopy, mammography and differential angiography. Also, the method of the invention is effective in computed axial tomography (CAT).

DETAILED DESCRIPTION OF THE INVENTION

Figure 1:
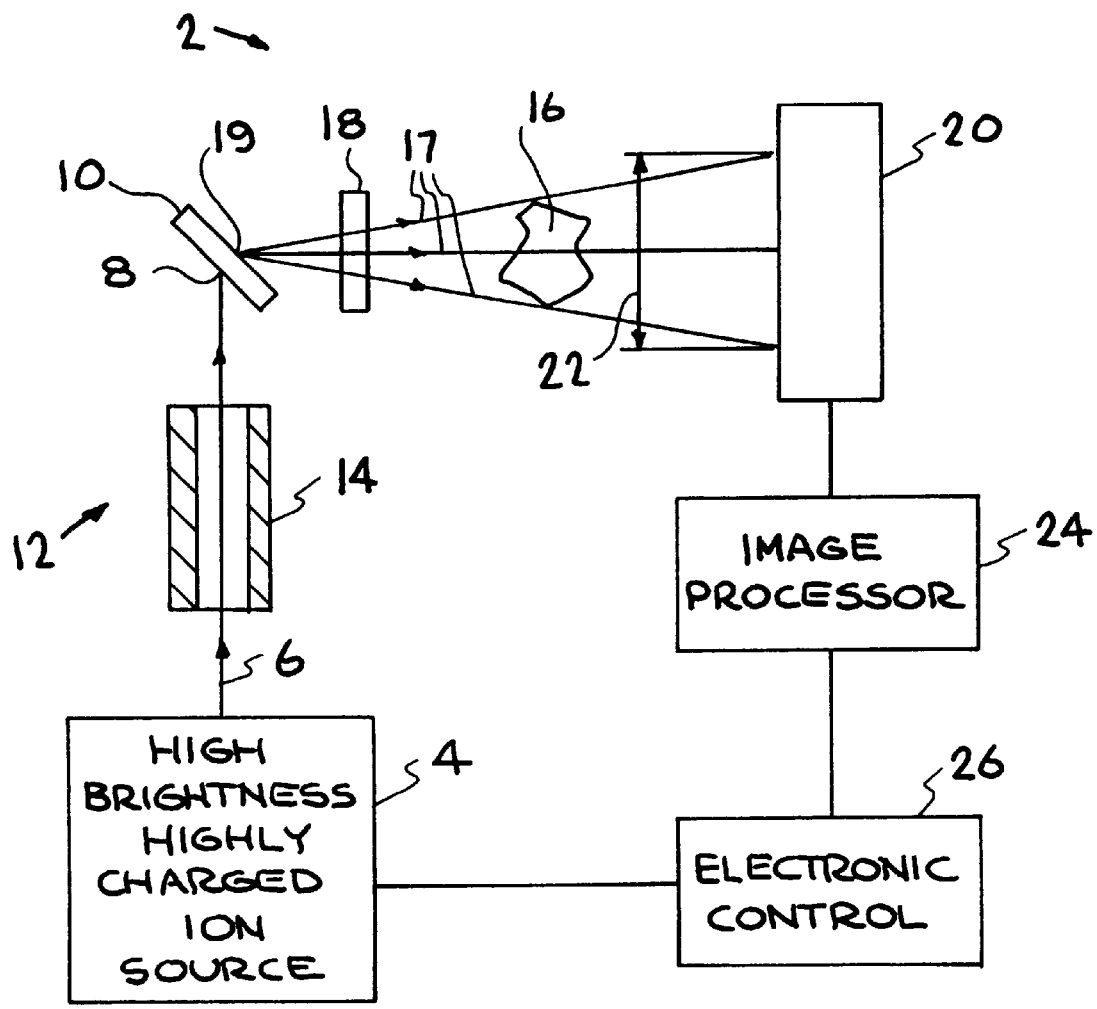
FIG. 1 is a schematic overall view of the imaging system of the present invention.

Referring to FIG. 1, an x-ray imaging system 2 illustrating the present invention indicates a system encompassing a high brightness highly-charged-ion source 4 able to supply a flux of ions 6 that can be focused to an ion spot 8 on an x-ray production target 10, with the ions having a charge state appropriate for emission of x rays of a desired energy, and with the ions having sufficiently low energy so that they do not penetrate deeply into the target. Common targets include beryllium and aluminum. Any ion source providing highly charged ions is suitable for the present invention, particularly a source capable of emitting a high flux of ions with high brightness. The brightness of the ion beam is the flux of ions divided by the emittance squared. Usually the ion source is an EBIS or EBIT that provides an absolute emittance for the slow highly charged ions of less than 5, and preferably less than about 1.5, and most preferably about 0.1 to about 1.2 pi mm mrad (calculated at 30 kV acceleration potential). One preferred source of the slow highly charged ions 6 is an EBIT as described by R. E. Marrs, et al. in *Physics Today*, October 1994, pp. 27–34, the disclosure of which is incorporated by reference herein in its entirety. More preferred sources of the slow highly charged ions include modified embodiments of the above-described EBIT that exhibit increased intensity and brightness. Modified EBIT embodiments can include (1) an increased size and current of the electron gun, (2) an increased electron emission per unit area of the cathode of the gun, (3) an increased magnetic field used to compress the electron beam, (4) an increased length of the ion trap, (5) a separation between the trapped highly charged ions and any neutral species injected into the trap, and (6) extracted ions from the source having their emittance reduced by evaporative cooling. The slow highly charged ions produced from such sources normally have energies of less than 1 MeV/u, preferably less than 0.1 MeV/u, and most preferably in the range from about 0.01 to about 0.06 MeV/u.

Elements with atomic numbers up to 92, normally above 6, and preferably from about 30 to 60, encompass highly charged ions 6 from source 4. The highly charged ions have a charge of greater than 3+. Examples of preferred highly charged ions include fully stripped ions or ions containing one or relatively few electrons. Examples of a preferred ion charge state include Ar 17+, Ar 18+, Kr 35+, Kr 36+, Mo 41+, Mo 42+, I 52+, I 53+, Xn 53+, Xn 54+, La 56+and La 57+. An ion focusing system 12, including lens apparatus 14, as is described by R. E. Marrs, et al., in *Rev. Sci. Instrum.* vol. 69, p. 204 (1998), effects a convergence of the stream of ions 6 so as to focus the ions on the relatively small ion spot 8, which is usually less than 100 microns, and preferably from about 10 to about 100 microns, FWHM. When the invention is applied to mammography, the spot size is preferably from about 10 to about 75, and most preferably from about 40 to about 60 microns, FWHM. In an application to angiography, the spot size is normally in the range from about 50 to about 100 microns, and preferably from about 65 to about 85 microns, FWHM. Although a spot size of about 20 microns is utilized in an x-ray microscope embodiment of the invention disclosed hereinafter in the example, the spot size for x-ray microscopic purposes is usually about 0.1 to about 10 microns FWHM.

Referring still to FIG. 1, x-rays 17 are emitted from ions at target 10 and can optionally and preferably pass through a filter 18 suitable for attenuating unwanted portions of the x-ray spectrum prior to passage through specimen 16. X-rays 17 are emitted from an x-ray emission spot 19 having essentially the same spot size as that of ion spot 8. The specimen 16 is located between the target 10 and an x-ray detector 20. Ion source 4, ion focusing system 12, and target 10 are preferably enclosed in a vacuum; however, a specimen 16 through which the x-rays pass, may be located in air. A preferred detector is an electronic digital imaging detector, such as a photon counting array detector such as described in P. Datte et al. in *Nuclear Instruments and Methods A* vol. 391, p. 471 (1997). Other preferred electronic digital imaging detectors include, for example, amorphous silicon, which is available commercially, amorphous selenium, cadmium-zinc-telluride, or other types of electronic detectors. Still another example of a detector is a scintillator or fluorescent screen in combination with a charge-coupled device, i.e., CCD, or other type of camera. Of course, another detector includes x-ray film.

The specimen can preferably be placed closer to the x-ray source than to the detector so that an image 22 (e.g., projected image) of the specimen is magnified by projection onto detector 20. In this manner, the resolution of image 22, particularly an enlarged image, is greater than the resolution capabilities of detector 20. For example, a specimen resolution of 100 microns may be obtained with a detector having 500-micron pixel size. The projection is derived from an x-ray emission spot of less than 100-micron size (FWHM). In one embodiment of the present invention, x-rays from an x-ray emission spot size of order 1-micron are passed through a small specimen having a size of order 1-mm which is placed at a distance of order 1 mm from the x-ray emission spot so as to provide a functional x-ray microscope with a resolution of order 1-micron. It will be understood by those of ordinary skill in the art that wide ranges of resolution and magnification are possible.

In a preferred embodiment of the invention illustrated in FIG. 1, image 22 from x-ray detector 20 is transmitted to an image processor 24 via means that are electronic, digital, fluorescent, or the like. The processed image can be modified, stored, transmitted, i.e., further processed, with an electronic control 26. Such a control may also be used to change (switch) the type of slow highly charged ions 6 (i.e., ions of different atomic number) produced in source 4 so that the energy of x-rays 17 is changed if desired. The electronic control 26 is also used to preserve separate x-ray images for the different x-ray energies. The images obtained at different x-ray energies may be compared so as to enhance features associated with a specific element. Thus, wavelengths (and corresponding photon energy) of monochromatic x-rays 17, derived from characteristic transitions in the slow highly charged ions of one or more specific elements, can be predetermined and exposed to specimen 16, and such x-rays subsequently detected. For example, microcalcifications in mammography could be enhanced by comparing images obtained at 18-keV with x-rays from Mo 42+ and at 30 keV with x-rays from Xe 54+, and vascular imaging could be enhanced by comparing images obtained at 32-keV with x-rays from Cs 54+ and at 34 keV with x-rays from La 56+. Switching, particularly rapid switching, between two or more charged ions of different atomic numbers, provides enhanced image resolution.

In a preferred embodiment referring to FIG. 1, a source of slow highly charged ions 6 having energies of less than about 1 MeV/u is still capable of producing a flux of ions that generate at least $1\times10^5$ x-ray photons/sec, and preferably at least $1\times10^9$ x-ray photons/sec, isotropically. Specimen 16 is placed at a 10 cm distance from x-ray production target 10 which is placed at a 50 cm distance from detector 20 having a 1000×1000 pixel display of 0.5 mm pixel size which projects down to 100 microns at specimen 16 with a 10 cm×10 cm field of view. At an intensity of $1\times10^9$ x-ray photons/sec, the specimen receives an x-ray flux of $8\times10^3$ photons/mm$^2$s. High efficiency detectors, such as photon counting arrays, in combination with the monochromatic character of the x-rays, allow about 10 to about 1000 times fewer photons to produce an image 22 of equivalent quality (i.e., resolution) to that of images from conventional apparatus . Hence, in most applications of the imaging system, the exposure dose of the x-rays 17 with specimen 16 may be reduced about 10 or more times for equivalent resolution to that obtained from conventional apparatus. The projection geometry reduces the fraction of scattered x-rays reaching the detector, thereby further improving the quality of the x-ray image and reducing the exposure dose. Either a substantially reduced radiation dose for equivalent resolution to conventional sources or a much improved resolution with an equivalent dose can be readily achieved by the apparatus and method of the invention.

An advantage of the present invention is a greatly reduced heating of the x-ray production target compared to a conventional x-ray tube. Such reduced heating results from: (1) a lower x-ray dose being required to obtain an image, (2) a higher radiation efficiency for slow highly charged ions as compared to electron beams, and (3) nearly all x-ray photons have the desired energy (i.e., the spectrum is monochromatic). Another advantage of the present invention is that the range and scattering of slow highly charged ions are far less than that of electrons in a conventional x-ray tube. Thus, beam spreading does not limit resolution of images detected by the present invention. Furthermore, x-ray emission occurs within a few nanometers of the target surface.

Figure 2A:
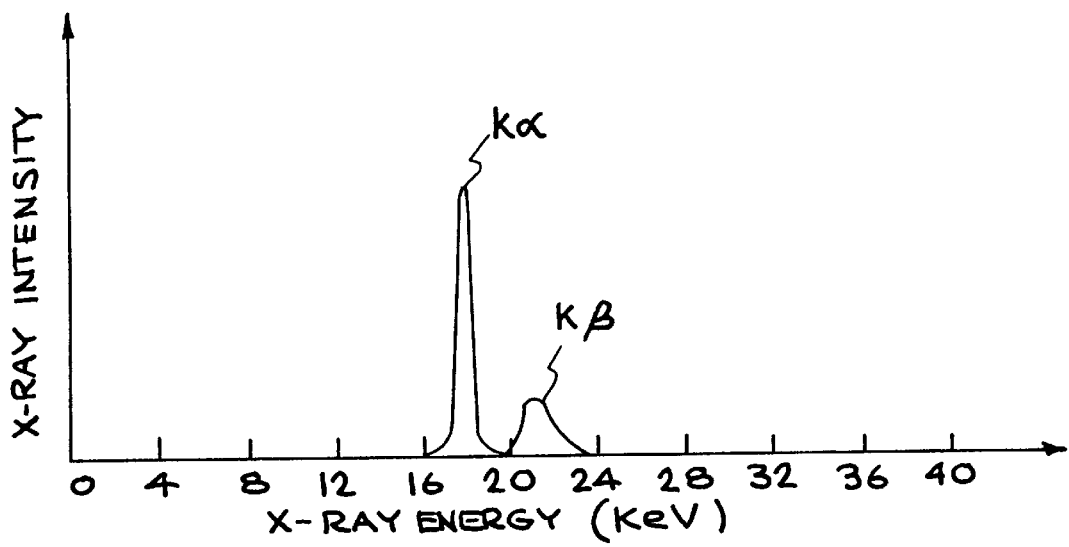
FIG. 2 illustrates the x-ray spectrum obtained from a highly-charged-ion device compared to the spectrum obtained from a conventional x-ray tube.
Figure 2B:
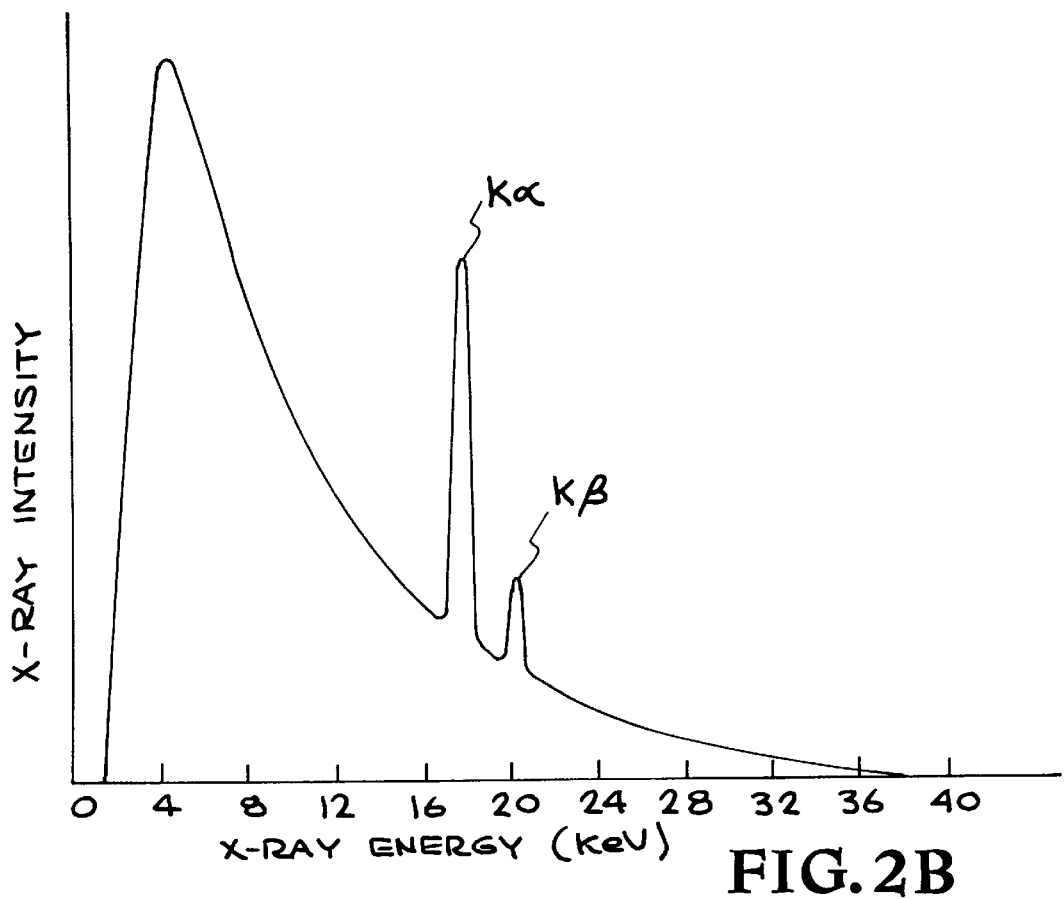

FIG. 2A illustrates an x-ray spectrum obtained with the present invention. The energies of the x-rays fall primarily into two groups labeled Kα and Kβ. Such an exemplary narrow band of x-rays has been referred herein as "monochromatic x-ray radiation." FIG. 2B illustrates an x-ray spectrum wherein a broad x-ray energy distribution (i.e., continuum x-ray spectrum) is produced by conventional x-ray tubes. Such a broad spectrum does not allow suitable resolution or contrast of an image. The narrow energy spread illustrated in FIG. 2A of the x-rays derived from the slow highly-charged ions used in the present invention encompasses essentially no continuum x-ray radiation. Referring to FIG. 2A and 2B, the energy scale is such that the x-rays originate from highly-charged-ions of molybdenum (FIG. 2A) or from a molybdenum anode of a conventional x-ray tube (FIG. 2B). Portions of the x-ray spectrum can be attenuated with absorption filters, such as filter 18 in FIG. 1. For example, the use of a Kedge filter chosen such that the absorption edge lies between peaks Kα and Kβ can be used to substantially reduce the intensity of Kβ with minimal affect on Kα, further narrowing the energy distribution from the source.

Figure 3:
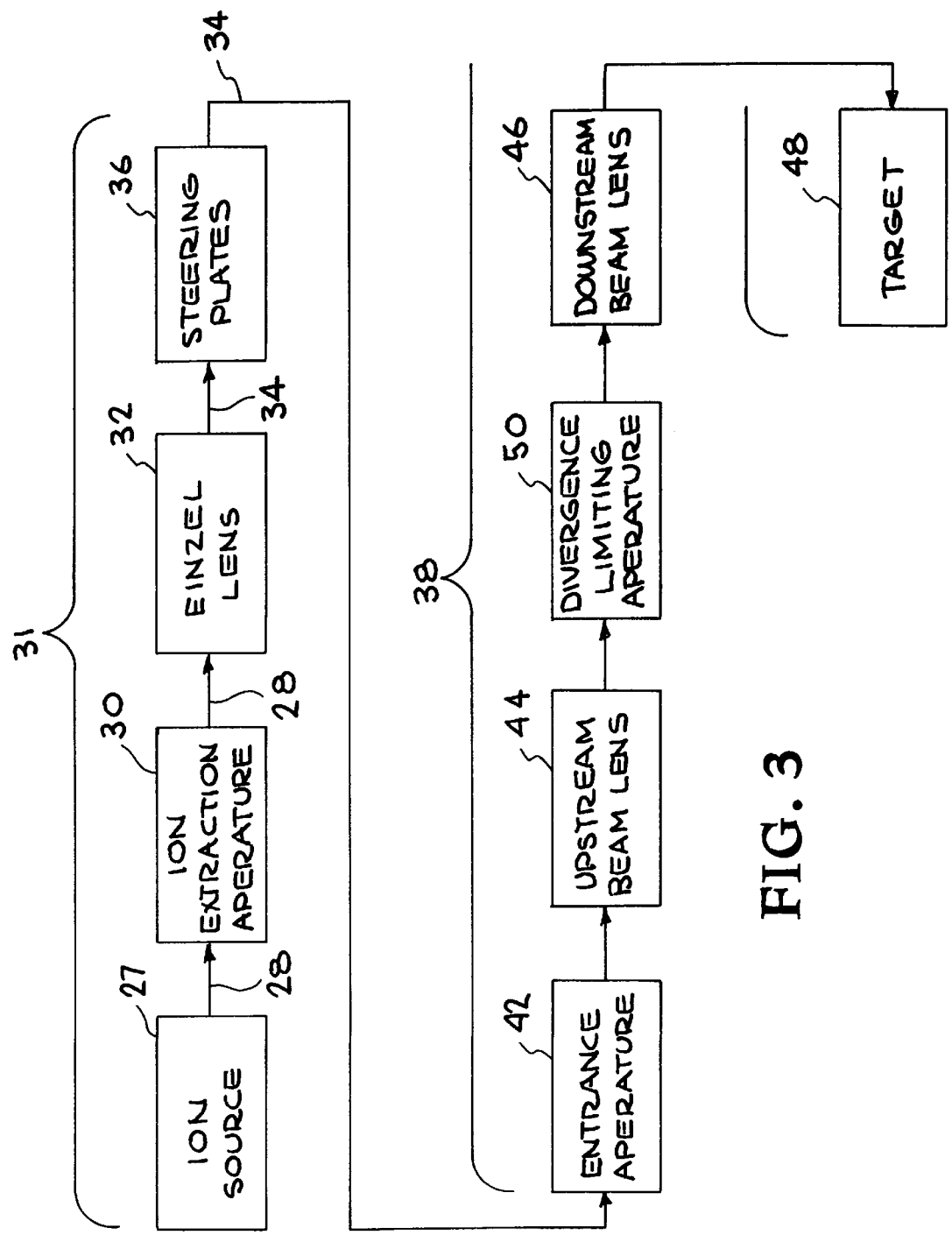
FIG. 3 is a block diagram of a focusing apparatus for transporting slow highly charged ions from a source and focusing them to a small spot.

FIG. 3 illustrates an example of an ion focusing device or system for producing small x-ray emission spots, usually those of spot size less than 250 microns, and particularly less than about 100 microns. In general, an ion beam 34 is extracted using ion beam extraction optics, shown generally as 31, and focused upon a production target 48 by an ion focusing column, shown generally as 38. From an ion source shown generally as 27, ions 28 exit from the source through an ion extraction aperture 30 after which they pass through an einzel lens 32 that focuses the ion beam 34, with the optional assistance of steering plates 36 used to correct minor misalignments of the apparatus, to a waist at the entrance of the final ion focusing column 38. Although any means for receiving and focusing a flux of ions as described herein may be employed, a representative embodiment includes an entrance aperture 42 at the entrance of focusing column 38 that defines and limits the size of ion beam 34. Focusing column 38 contains two einzel lenses, e.g., upstream beam lens 44 and downstream beam lens 46, which act together to produce a demagnified image of the entrance aperture at a sample such as an x-ray production target 48. The x-ray production target may preferably consist of a beryllium or aluminum vacuum window. A divergence limiting aperture 50 may be used to reduce aberrations inherent in the focusing lenses. Smaller ion spot sizes may be obtained at the expense of ion intensity by changing apertures and other ion optical elements. Those skilled in the art will understand the functions of the lenses, apertures, and steering plates, etc., and will understand that equivalent types of ion optical devices may also be employed.

The invention is further illustrated by the following example which is illustrative of a specific mode of practicing the invention and is not intended as limiting the scope of the invention as defined in the appended claims.

EXAMPLE

The following illustrates an x-ray microscope embodiment of the present invention.

Arrangement of the Microscope Embodiment

Referring to FIG. 1, the invention operates as a microscope when the size of the specimen and the distance of the specimen from the x-ray production target are both small. The magnification is represented by M=b/a, where a is the distance from the x-ray source to a specimen and b is the distance from the x-ray source to the detector, e.g., a CCD. The magnification is easily adjusted by varying the position of the specimen. In this example a=5 mm, b=50 mm, and M=10. The principles of a projection x-ray imaging system also apply to the x-ray microscope described herein.

The resolution of a microscope or imaging system is ultimately limited by the wavelength of the radiation used to form an image. This limit is commonly referred to as the diffraction limit. In principle, the resolution of an x-ray microscope can be much better than the resolution of a visible-light microscope because x rays have much shorter wavelengths than visible light. However no x-ray microscope or imaging system has approached the wavelength limit. The resolution of the present microscope arrangement is determined by the size of the focused ion spot, as for example, 20 $\mu$m for the results described herein. The contribution of diffraction to the image resolution is represented by $\Delta=(\lambda a)^{1/2}$, where $\lambda$ is the x-ray wavelength and a is the distance between the specimen and the x-ray source. In this example monochromatic x-ray radiation at approximately 3-keV energy is obtained from the recombination of $Ar^{18+}$ and $Ar^{17+}$ ions on a beryllium target foil. The x-rays are emitted isotropically from an ion recombination point. For 3 keV x-rays and $\alpha=5$ mm as in the present embodiment, $\Delta=1.4$ microns. If submicron focused ion spots are used, the effect of x-ray diffraction can be reduced by decreasing the specimen distance.

Ion Source

In this example, ions are obtained from an EBIT. In the EBIT used for the present example, a 150 mA electron beam is compressed to a diameter of 70 microns by a 3 T magnetic field. The ions are confined to a 2 cm length of the electron beam by voltages applied to three trap electrodes. Argon ions are produced from neutral argon gas injected into the trap. Trapped ions are quickly stripped to high charge states by successive ionizing collisions with beam electrons. More detailed descriptions of the EBIT and its extracted ion beams can be found in the *Physics Today* reference disclosed hereinbefore.

Ions are extracted from the EBIT by slowly raising the potential of the center trap electrode until the ions spill over one of the end electrodes, which is biased at a potential of 17.3 kV. The ions are then guided by the electron beam as far as the electron collector. After passing an extraction aperture, the slightly diverging ion beam is focused onto the entrance of the ion focusing column by an einzel lens as indicated in FIG. 3.

Ion Focusing

The components of the ion focusing column are selected to take advantage of the low emittance of EBIT ions to produce a relatively small focused ion spot for the microscope example. Referring to FIG. 3, the entrance aperture is a tantalum disk with a 0.5-mm-diameter hole. Each of the two einzel lenses produces a demagnified image of the entrance aperture. The amount of demagnification depends on the ion energy and the voltages applied to the einzel lenses. For the present measurements, each lens demagnifies the image by a factor of roughly 5. A 4-mm-diameter aperture is placed in front of the second lens to limit the off-axis position of ions entering this lens. The effect of this aperture is to limit spherical aberrations by removing ions with a large divergence angle. Note that ions in different charge states follow identical trajectories through the electrostatic lenses. Although some lower-charge-state ions are present in the beam, only $Ar^{18+}$ and $Ar^{17+}$ ions contribute to argon K x-ray production. Approximately $1\times10^6$ $Ar^{18+}$ and $Ar^{17+}$ ions are focused onto the target foil in a spot of diameter 20-microns FWHM. The energy of the ions at the target foil is 17.3 q keV, where q is the ion charge.

Microscope Performance

Figure 4:
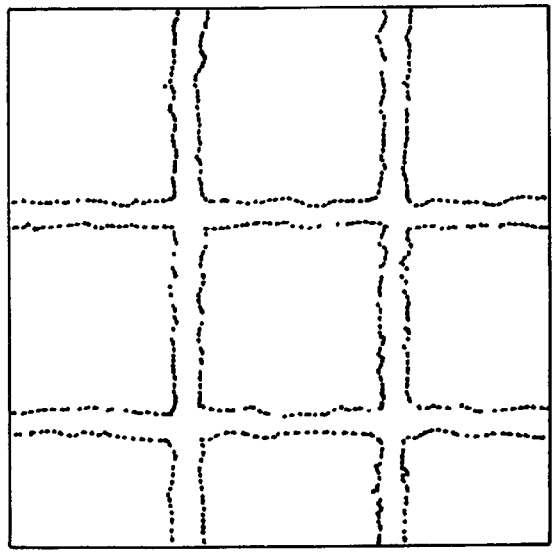
FIG. 4 is an image collected with 3 keV x-rays of a metallic mesh having a spacing of the mesh lines of 500 microns.

In the present example, x-rays are detected with a 512×512 pixel CCD camera. The CCD is thinned and back-illuminated for sensitivity to soft x-rays, and the pixel size is 25 microns. A 100-micron-thick beryllium vacuum window in front of the CCD allows the CCD chip to operate in vacuum so that it can be cooled during image acquisition. An electroformed nickel mesh with 70-micron-wide lines on 500 micron centers is used to test the performance of the microscope. The thickness of the nickel mesh is 4.7 microns, corresponding to a transmission of 8% for 3.1 keV argon K$\alpha$ x rays. An x-ray image of the nickel mesh from a two-hour exposure is shown in FIG. 4. The intensity of each pixel is the integral of the charge it collects from multiple x-ray events during the exposure time. The noise in the image is from x-ray photon statistics and can be reduced with a longer exposure time. The contribution of electronic noise from the CCD is negligible.

Figure 5:
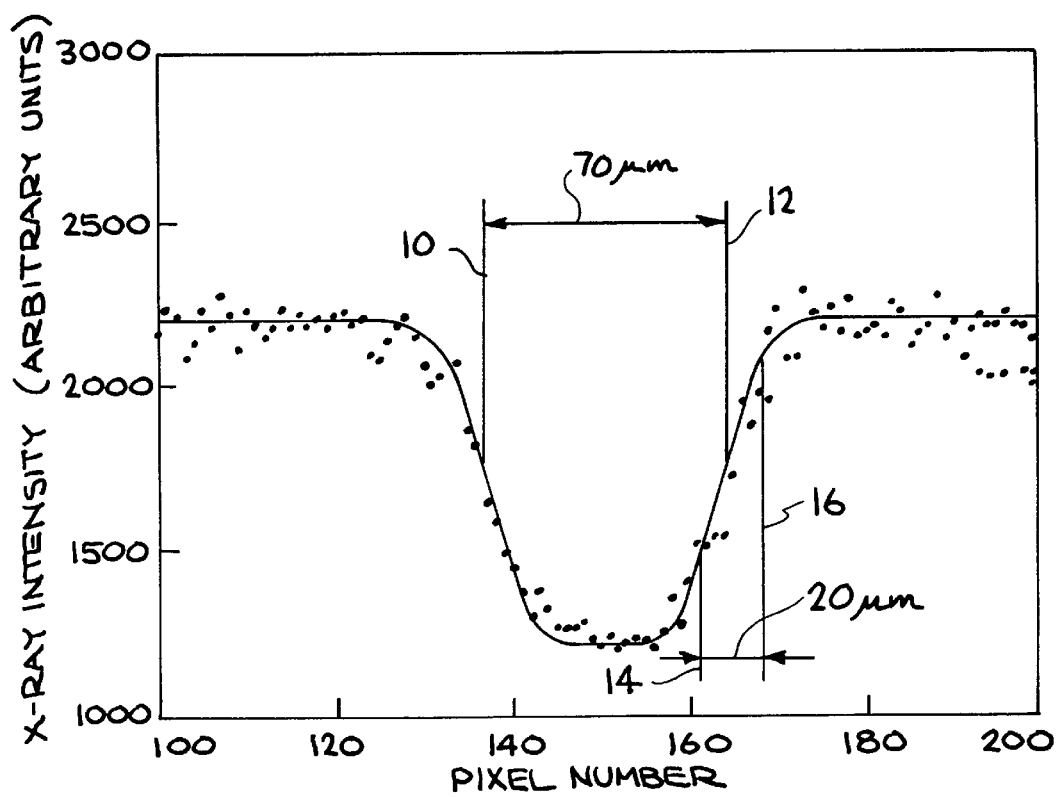
FIG. 5 is a profile of one of the mesh lines in the image of FIG. 4. The solid curve is a fit with the x-ray source size adjusted to match the measured profile.

The blurring of the edges of the mesh lines in the x-ray image is used to obtain an estimate of the resolution of the x-ray microscope. FIG. 5 shows a profile from one of the mesh lines of FIG. 4 obtained by averaging over 100 rows in the CCD image. Since the nickel-mesh specimen is much closer to the x-ray source than to the CCD, the resolution of the microscope is approximately equal to the width of the focused ion spot. If the focused ion spot has a Gaussian intensity profile with cylindrical symmetry, as expected, then each edge of a mesh line has an error-function profile. The solid curve in FIG. 5 is calculated using a Gaussian beam profile with its width adjusted to fit the observed image. The curve indicates a 70 micron wide line for the mesh illustrated by the separation between lines 10 and 12 in FIG. 5. The 20 micron resolution is illustrated by the separation between lines 14 and 16 indicated by the slope of the edge. The resulting value for the diameter of the x-ray-emitting spot is 20 microns full width at half maximum (FWHM).

Although particular embodiments of the present invention have been described and illustrated, such is not intended to limit the invention. Modifications and changes will no doubt become apparent to those skilled in the art, and it is intended that the invention only be limited by the scope of the appended claims.

What is claimed is:

1. A radiographic imaging device comprising:
   a source of x-ray radiation generated from the deexcitation of slow highly charged ions at the surface of a target; and
   a detector for detecting said x-ray radiation from said source subsequent to said radiation passing through a specimen.

2. The device of claim 1 wherein said x-ray radiation from said source having a spot size in the range between 0.1 and 250 microns, full width at half maximum (FWHM).

3. The device of claim 1 wherein said detector adapted to receive an enlarged projected image of said specimen.

4. The device of claim 1 wherein said target comprises beryllium or aluminum.

5. The device of claim 1 wherein said source is capable of providing an intensity for said slow highly charged ions to generate greater than $1\times10^5$ x-ray photons/sec.

6. The device of claim 1 wherein said source is capable of providing an emittance for said slow highly charged ions of less than 5 pi mm mrad, calculated at 30 kV acceleration potential.

7. The device of claim 1 wherein said detector comprises an electronic digital imaging detector.

8. The device of claim 1 wherein said detector is capable of counting individual photons.

9. The device of claim 1 wherein a filter is located between said target and said specimen.

10. The device of claim 1 wherein said radiation comprises x-ray monochromatic radiation characteristic of transitions in said slow highly charged ions.

11. The device of claim 10 wherein said source further comprises means for switching between at least two of said highly charged ions having different atomic numbers.

12. The device of claim 2 adapted for x-ray microscopy and wherein said spot size has a range from about 0.1 to about 10 microns.

13. The device of claim 2 adapted for mammography and wherein said spot size has a range from about 10 to about 75 microns.

14. The device of claim 2 adapted for angiography and wherein said spot size has a range from about 50 to about 100 microns.

15. A radiographic imaging device comprising:

a target for impingement by slow highly charged ions;

a source of said slow highly charged ions that are capable of deexcitation at a surface of said target to generate x-ray monochromatic radiation and said source adapted for focusing a spot size of said radiation from about 10 to about 100 microns, full width at half maximum (FWHM); and an imaging detector for detecting said x-ray monochromatic radiation from said target subsequent to said radiation passing through a specimen.

16. The device of claim 15 wherein said source and said surface of said target adapted to project an enlarged image of at least a portion of said specimen onto more than one pixel volume of said detector.

17. The device of claim 15 wherein said source is capable of providing an intensity for said slow highly charged ions to generate greater than $10^8$ x-ray photons/sec.

18. The device of claim 15 wherein said source is capable of providing an emittance for said slow highly charged ions of less than 1.5 pi mm mrad, calculated at 30 kV acceleration potential.

19. The device of claim 15 wherein a filter is located between said target and said specimen and said detector is a electronic imaging detector.

20. The device of claim 15 wherein said source further comprises means for switching between at least two of said highly charged ions having different atomic numbers.

21. A radiographic imaging device comprising:

a source of a beam of slow highly charged ions from an electron beam ion source or trap;

a focusing column for reducing a spot size of said beam;

a target upon which said ions of said beam deexcite to generate x-ray monochromatic radiation; and an imaging detector for detecting said x-ray monochromatic radiation emitted from said target subsequent to said radiation passing through a specimen.

22. The device of claim 21 adapted for mammography and wherein said x-ray monochromatic radiation from said target having a spot size in the range between 40 and 60 microns, full width at half maximum (FWHM).

23. The device of claim 21 adapted for angiography and wherein said x-ray monochromatic radiation from said target having a spot size in the range between 65 and 85 microns, full width at half maximum (FWHM).

24. The device of claim 21 wherein said imaging detector adapted for detecting an enlarged projected image of at least a portion of said specimen.

25. The device of claim 21 wherein said source is capable of providing an intensity for said slow highly charged ions to generate greater than about $10^9$ x-ray photons/sec.

26. The device of claim 21 wherein said source is capable of providing an emittance for said slow highly charged ions from about 0.1 to about 1.2 pi mm mrad calculated at 30 kV acceleration potential.

27. The device of claim 21 wherein said imaging detector is capable of detecting a radiograph having smaller resolution than an single pixel volume of said imaging detector.

28. The device of claim 21 wherein a filter is located between said target and said specimen and said imaging detector is a electronic digital imaging detector.

29. The device of claim 21 wherein said source further comprises means for switching between at least two of said highly charged ions having different atomic numbers.

30. The device of claim 21 wherein said source is capable of imparting less than 1 MeV/u to said slow highly charged ions.

31. The device of claim 21 wherein said source is capable of imparting a charge of greater than 3+ to said slow highly charged ions of said beam.

32. A method for producing a radiographic image, said method comprising:

(1) positioning a specimen for exposure;

(2) exposing said specimen to radiation generated from the deexcitation of slow highly charged ions;

(3) detecting said radiation subsequently to said radiation passing through at least a portion of said specimen.

33. The method of claim 32 further comprising projecting an image from said specimen to an imaging detector.

34. The method of claim 33 wherein said image is enlarged.

35. The method of claim 32 wherein said detector of given pixel size generates a smaller resolution to said image than said given pixel size.

36. The method of claim 32 wherein said radiation comprises x-ray monochromatic radiation.

37. The method of claim 36 wherein a predetermined wavelength of said radiation is exposed to said specimen.

38. The method of claim 37 further comprising periodically switching between at least two predetermined wavelengths of said radiation.

39. The method of claim 36 wherein said image comprises a differential angiographic image.

40. The method of claim 36 wherein said image comprises an x-ray microscopic image.

41. The method of claim 36 wherein said image comprises a mammographic image.

42. A method for producing a radiographic image, said method comprising:

(1) positioning a specimen for exposure;

(2) exposing said specimen to a predetermined x-ray monochromatic radiation generated from the deexcitation of slow highly charged ions and having a spot size from about 10 to about 100 microns;

(3) detecting said radiation with a electronic digital imaging detector subsequently to said radiation passing through at least a portion of said specimen.

43. The method of claim 42 producing a mammographic image and wherein said x-ray monochromatic radiation from said target having a spot size in the range between 40 and 60 microns, full width at half maximum (FWHM).

44. The method of claim 42 producing an angiographic image and wherein said x-ray monochromatic radiation from said target having a spot size in the range between 65 and 85 microns, full width at half maximum (FWHM).

45. The method of claim 42 wherein said electronic imaging detector detecting an enlarged projected image of at least a portion of said specimen.

46. The method of claim 42 wherein said source providing a sufficient intensity for said slow highly charged ions to generate greater than about $10^9$ x-ray photons/sec.

47. The method of claim 42 wherein said source providing an emittance for said slow highly charged ions from about 0.1 to about 1.2 pi mm mrad calculated at 30 kV acceleration potential.

48. The method of claim 42 wherein said imaging detector is capable of detecting a radiograph having smaller resolution than an single pixel volume of said electronic digital imaging detector.

49. The method of claim 42 wherein a filter is located between said target and said specimen.

50. The method of claim 42 further comprising switching between at least two of said highly charged ions having different atomic numbers.

51. The method of claim 42 wherein said source imparting less than 1 MeV/u to said slow highly charged ions.

52. An ion beam focussing apparatus comprising:

means for receiving an ion beam having a flux greater than $10^8$ ions per second;

at least one lens for focusing said ion beam to a spot size of less than 100 microns FWHM; and means for projecting said ion beam to a target.

* * * * *